US009260706B2

(12) United States Patent
Wieland et al.

(10) Patent No.: US 9,260,706 B2
(45) Date of Patent: Feb. 16, 2016

(54) PERFORMANCE-ENHANCED PROTEASE VARIANTS

(71) Applicant: Henkel AG & Co. KGaA, Duesseldorf (DE)

(72) Inventors: Susanne Wieland, Zons/Dormagen (DE); Petra Siegert, Haan (DE); Timothy O'Connell, Duesseldorf (DE); Karl-Heinz Maurer, Erkrath (DE); Ronny Martinez, Aachen (DE); Ulrich Schwaneberg, Kelmis-Hergenrath (BE); Hendrik Hellmuth, Duesseldorf (DE)

(73) Assignee: HENKEL AG & CO. KGAA, Dusseldorf (DE)

( * ) Notice: Subject to any disclaimer, the term of this patent is extended or adjusted under 35 U.S.C. 154(b) by 2 days.

(21) Appl. No.: 14/020,991

(22) Filed: Sep. 9, 2013

(65) Prior Publication Data
US 2014/0017763 A1    Jan. 16, 2014

Related U.S. Application Data

(63) Continuation of application No. PCT/EP2012/053659, filed on Mar. 2, 2012.

(30) Foreign Application Priority Data

Mar. 10, 2011  (DE) .................... 10 2011 005 354

(51) Int. Cl.
C12N 9/54      (2006.01)
C11D 3/386     (2006.01)

(52) U.S. Cl.
CPC  *C12N 9/54* (2013.01); *C11D 3/386* (2013.01); *C11D 3/38609* (2013.01); *C11D 3/38618* (2013.01)

(58) Field of Classification Search
CPC ...................................................... C12N 9/54
See application file for complete search history.

(56) References Cited

U.S. PATENT DOCUMENTS

| 6,777,218 | B1 | 8/2004 | Mikkelsen et al. |
| 2005/0003504 | A1 | 1/2005 | Weber et al. |
| 2005/0113273 | A1 | 5/2005 | Weber et al. |
| 2013/0005637 | A1 | 1/2013 | Siegert et al. |

FOREIGN PATENT DOCUMENTS

| DE | 102006022216 A1 | 11/2007 |
| EP | 1025241 B1 | 3/2005 |
| EP | 1553174 A2 | 7/2005 |
| WO | 2007/131657 A2 | 11/2007 |
| WO | 2009/121725 A1 | 10/2009 |

OTHER PUBLICATIONS

PCT International Search Report (PCT/EP2012/053659) dated Apr. 17, 2012.
Gornall et al., "Determination of Serum Proteins by Means of the Biuret Reaction", Journal of Biological Chemistry, vol. 177, pp. 751-766, 1948.
Bender et al., "The Determination of the Concentration of Hydrolytic Enzyme Solutions: a-Chymotrypsin, Trypsin, Papain, Elastase, Subtilisin, and Acetylcholinesterase", Journal of the American Chemical Society, vol. 88:24, pp. 5890-5913, 1966.
Van Raay et al, "The Determination of Proteolytic Activity in Enzyme Concentrates and Enzyme Containing Detergents", Tenside Detergents, vol. 7, No. 3, pp. 125-132, 1970.
Delmar et al., "A Sensitive New Substrate for Chymotrypsin", Analytical Biochemistry, vol. 99, pp. 316-320, 1979.
Kawamura et al., "Construction of a Bacillus subtilis Double Mutant Deficient in Extracellular Alkaline and Neutral Proteases", Journal of Bacteriology, vol. 160, No. 1, pp. 442-444, 1984.
Altschul et al., "Basic Local Alignment Search Tool", Journal of Molecular Biology, vol. 215, pp. 403-410, 1990.
Siezen, "Subtilases: Subtilisin-like Serine Proteases", Subtilisin Enzymes: Practical Protein Engineering, pp. 75-93, Plenum Press, New York, 1996.
Altschul et al., "Gapped BLAST and PSI-BLAST: A New Generation of Protein Database Search Programs", Nucleic Acids Research, vol. 25, No. 17, pp. 3389-3402, 1997.
Notredame et al., "T-Coffee: A Novel Method for Fast and Accurate Multiple Sequence Alignment", Journal of Molecular Biology, vol. 302, pp. 205-217, 2000.
Gupta et al., "Bacterial Alkaline Proteases: Molecular Approaches and Industrial Applications", Applied Microbiology and Biotechnology, vol. 59, pp. 15-32, 2002.

(Continued)

*Primary Examiner* — Sheridan Swope
(74) *Attorney, Agent, or Firm* — Steven L. Nichols; Fabian Vancott

(57) ABSTRACT

Proteases encompassing an amino acid sequence, which are at least 70% identical to the amino acid sequence specified in SEQ ID NO. 1 over the entire length thereof and which, in the listing according to SEQ ID NO. 1, have the amino acid substitution I21V in combination with at least one further amino acid substitution, the further amino acid substitution being selected from the group consisting of Q12L, M122L, N177V, A222S, V228I and T247N, and agents encompassing such proteases, exhibit very good cleaning performance on egg-containing stains.

14 Claims, 1 Drawing Sheet

(56) References Cited

OTHER PUBLICATIONS

Chenna et al., "Multiple Sequence Alignment with the Clustal Series of Programs", Nucleic Acids Research, vol. 31, No. 13, pp. 3497-3500, 2003.

Wong et al., "Sequence Saturation Mutagenesis (SeSaM): A Novel Method for Directed Evolution", Nucleic Acids Research, vol. 32, No. 3, e26, 2004.

```
                          1                                                50
SEQ ID NO. 1    (1)  QQTVPWGITRVQAPTVHNRGITGSGVKVAILDTGIAQHSDLTIRGGASFV
SEQ ID NO. 2    (1)  QQTVPWGITRVQAPTVHNRGVTGSGVKVAILDTGIAQHSDLTIRGGASFV
SEQ ID NO. 3    (1)  AQSVPWGISRVQAPAAHNRGLTGSGVKVAVLDTGISTHPDLNIRGGASFV
                         51                                               100
SEQ ID NO. 1   (51)  PGESTTADLNGHGTHVAGTVAALNNSIGVIGVAPSADLYAVKVLGANGRG
SEQ ID NO. 2   (51)  PGESTTADLNGHGTHVAGTVAALNNSIGVIGVAPSADLYAVKVLGANGRG
SEQ ID NO. 3   (51)  PGEPSTQDGNGHGTHVAGTIAALNNSIGVLGVAPSAELYAVKVLGADGRG
                        101                                               150
SEQ ID NO. 1  (101)  SVSGIAQGLEWAATNNMHIANMSLGSDAPSTTLERAVNYATSRGVLVIAA
SEQ ID NO. 2  (101)  SVSGIAQGLEWAATNNMHIANMSLGSDAPSTTLERAVNYATSRGVLVIAA
SEQ ID NO. 3  (101)  AISSIAQGLEWAGNNGMHVANLSLGSPSPSATLEQAVNSATSRGVLVVAA
                        151                                               200
SEQ ID NO. 1  (151)  TGNNGTGSIGYPARYANAMAVGATDQNNRRASFSQYGTGIDIVAPGVGIQ
SEQ ID NO. 2  (151)  TGNNGTGSIGYPARYANAMAVGATDQNNRRASFSQYGTGIDIVAPGVGIQ
SEQ ID NO. 3  (151)  SGNSGASSISYPARYANAMAVGATDQNNRASFSQYGAGLDIVAPGVNVQ
                        201                                               250
SEQ ID NO. 1  (201)  STYLNNSYASMPGTSMATPHVAGVAALVKQKNPSWNATQIRNHLKNTATN
SEQ ID NO. 2  (201)  STYLNNSYASMPGTSMATPHVAGVAALVKQKNPSWNATQIRNHLKNTATN
SEQ ID NO. 3  (201)  STYPGSTYASLNGTSMATPHVAGAAALVKQKNPSWSNVQIRNHLKNTATS
                        251           269
SEQ ID NO. 1  (251)  LGNSSQFGSGLVNADAATR
SEQ ID NO. 2  (251)  LGNSSQFGSGLVNADAATR
SEQ ID NO. 3  (251)  LGSTNLYGSGLVNAEAATR
```

PERFORMANCE-ENHANCED PROTEASE VARIANTS

FIELD OF THE INVENTION

The present invention generally relates to enzyme technology, and more particularly relates to proteases and to the manufacture of proteases whose amino acid sequence has been modified, in particular with regard to the use thereof in washing and cleaning agents, to all sufficiently similar proteases having a corresponding modification, and to nucleic acids that code therefore. The invention further relates to methods and uses of said proteases and to agents containing them, in particular washing and cleaning agents.

BACKGROUND OF THE INVENTION

Proteases are among the most technically important enzymes of all. Their use in washing and cleaning agents has been established longer than that of any other enzymes, and they are contained in virtually all modern, high-performance washing and cleaning agents. They bring about the breakdown of protein-based stains on the item to be cleaned. Within this group, subtilisin-like proteases (subtilases, subtilopeptidases, EC 3.4.21.62), which because of the catalytically active amino acids are classed as serine proteases, are of particular importance. They act as non-specific endopeptidases and hydrolyze any acid amide bonds within peptides or proteins. Their pH optimum is usually in the distinctly alkaline range. A review of this family can be found for example in the article "Subtilases: Subtilisin-like Proteases" by R. Siezen, page 75-95 in "Subtilisin enzymes", edited by R. Bott and C. Betzel, New York, 1996. Subtilisases are naturally formed by microorganisms. Particularly worthy of mention as the most important group within the subtilases are the subtilisins that are formed and secreted by *Bacillus* species.

Examples of the subtilisin-like proteases that are preferably used in washing and cleaning agents are the subtilisins BPN' and Carlsberg, the protease PB92, the subtilisins 147 and 309, the protease from *Bacillus lentus*, in particular from *Bacillus lentus* DSM 5483, subtilisin DY and the enzymes thermitase, proteinase K and the proteases TW3 and TW7, which can be assigned to the subtilases but are no longer subtilisins in the narrower sense, as well as variants of the specified proteases which have a modified amino acid sequence as compared with the starting protease. Proteases are modified by methods known from the prior art, either selectively or randomly, and thus optimized for use in washing and cleaning agents, for example. Such methods include point mutagenesis, deletion or insertion mutagenesis or fusion with other proteins or protein components. Correspondingly optimized variants are thus known for most proteases that are known from the prior art.

The international patent application WO 03/054185 discloses an alkaline protease from *Bacillus gibsonii* (DSM 14391), including the use thereof in washing or cleaning agents. In accordance with the Budapest Treaty on the International Recognition of the Deposit of Microorganisms of 28 Apr. 1977, this strain was deposited with the Deutsche Sammlung von Mikroorganismen and Zellkulturen GmbH, InhoffenstraBe 7B, 38124 Braunschweig, Germany on 1 Mar. 2001 under the ID number 01-192 and accession number DSM 14391. In contrast to the aforementioned proteases, this protease has considerable differences in the amino acid sequence, such that an identity comparison of the amino acid sequences results in identity values of below 80%. In the case of the alkaline protease from *Bacillus gibsonii* (DSM 14391), only a few protease variants optimized for use in washing and cleaning agents have been known in the prior art thus far.

The object of the present invention is to further develop a protease of the alkaline protease from *Bacillus gibsonii* (DSM 14391) type or a sufficiently similar protease (based on the sequence identity) and to obtain protease variants which are suitable and advantageously improved for use in washing or cleaning agents.

The invention provides a protease encompassing an amino acid sequence, which is at least 70% identical to the amino acid sequence specified in SEQ ID NO. 1 over the entire length thereof and which, in the listing according to SEQ ID NO. 1, has the amino acid substitution I21V in combination with at least one further amino acid substitution, the further amino acid substitution being selected from the group consisting of Q12L, M122L, N177V, A222S, V228I and T247N.

The invention also provides a method for producing a protease, encompassing the introduction of an amino acid substitution I21V in combination with at least one further amino acid substitution, the further amino acid substitution being selected from the group consisting of Q12L, M122L, N177V, A222S, V228I and T247N, in the listing according to SEQ ID NO. 1, into a starting protease, which over the entire length thereof is at least 70% identical to the amino acid sequence specified in SEQ ID NO. 1.

A protease within the meaning of the present patent application therefore encompasses both the protease as such and also a protease produced by a method according to the invention. Therefore all references to protease relate both to the protease as a substance and to the corresponding methods, in particular production methods for the protease.

Further subject matters of the invention relate to the proteases according to the invention and to methods for producing proteases according to the invention, to nucleic acids that code for these proteases, to non-human host cells containing proteases or nucleic acids according to the invention, and to agents encompassing proteases according to the invention, in particular washing and cleaning agents, to washing and cleaning methods, and to uses defined by means of proteases according to the invention.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A protease encompassing an amino acid sequence, which is at least 70% identical to the amino acid sequence specified in SEQ ID NO. 1 over the entire length thereof and which, in the listing according to SEQ ID NO. 1, has the amino acid substitution I21V in combination with at least one further amino acid substitution, the further amino acid substitution being selected from the group consisting of Q12L, M122L, N177V, A222S, V228I and T247N.

A method for producing a protease, encompassing the introduction of an amino acid substitution I21V in combination with at least one further amino acid substitution, the further amino acid substitution being selected from the group consisting of Q12L, M122L, N177V, A222S, V228I and T247N, in the listing according to SEQ ID NO. 1, into a starting protease, which over the entire length thereof is at least 70% identical to the amino acid sequence specified in SEQ ID NO. 1.

BRIEF DESCRIPTION OF THE DRAWINGS

The present invention will hereinafter be described in conjunction with the following drawing figures, wherein like numerals denote like elements, and FIG. 1. Sequence comparison (alignment) of the sequences according to SEQ ID NO. 1, SEQ ID NO. 2 and SEQ ID NO. 3, created with the Vector NTI® Suite 10.3 program (Invitrogen Corporation, 1600 Faraday Avenue, Carlsbad, Calif., USA) using default parameters.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Surprisingly it has been found that a modification according to the invention of position 21 in conjunction with a modification of at least one of positions 12, 122, 177, 222, 228 and 247 in a protease encompassing an amino acid sequence that is at least 70% identical to the amino acid sequence specified in SEQ ID NO. 1 brings about an improved performance by this modified protease in washing and cleaning agents in comparison to a corresponding protease not having said modifications. This is particularly surprising since the protease that is modified according to the invention differs considerably from other subtilisins established in the prior art, such as for example subtilisin 309, PB92, the alkaline protease from *Bacillus lentus* DSM 5483 or BPN'. For example, a protease having SEQ ID NO. 1 is 78.4% identical to subtilisin 309, 78.1% identical to PB92, 77.7% identical to the alkaline protease from *Bacillus lentus* DSM 5483 and 55.3% identical to BPN', wherein SEQ ID NO. 1 discloses the sequence of the mature protease from *Bacillus gibsonii* (DSM 14391). Thus it could not have been anticipated that, for proteases of the alkaline protease from *Bacillus gibsonii* (DSM 14391) type for use in washing and cleaning agents, performance-enhanced protease variants are obtained by a modification at position 21 in conjunction with a modification of at least one of positions 12, 122, 177, 222, 228 and 247 in the numbering system for alkaline proteases from *Bacillus gibsonii* (DSM 14391), relative to the mature enzyme according to SEQ ID NO. 1.

For example, preferred embodiments of proteases according to the invention make such a good contribution to the cleaning performance of a washing or cleaning agent containing the protease, that said contribution comes close to and even exceeds in the case of some stains the contribution of a proteolytic enzyme established for that purpose to the cleaning performance of the agent. Proteases according to the invention thus allow an improved removal of at least one, preferably of a plurality of protease-sensitive stains on textiles and/or hard surfaces, such as dishes. Preferred embodiments of proteases according to the invention demonstrate particularly advantageous cleaning performances on egg-containing stains, for example on the stain
whole egg/pigment on cotton: product no. C-S-37 obtainable from CFT (Center For Testmaterials) B.V., Vlaardingen, Netherlands.

Thus dirt-specific proteases are provided by preferred embodiments of the present invention, whose cleaning performance is selectively advantageous in respect of a stain or of a plurality of stains of a similar type. The stain focus of preferred embodiments of proteases according to the invention in respect of egg-containing stains is thus improved.

Preferred embodiments of proteases according to the invention achieve such advantageous cleaning performances even at low temperatures of between 10° C. and 40° C., between 10° C. and 30° C. and between 10° C. and 25° C., for example at 20° C.

Furthermore, preferred embodiments of proteases according to the invention have a particular stability with regard to surfactants and/or bleaching agents and/or temperature influences, in particular with regard to high or low temperatures, and/or with regard to acid or alkaline conditions and/or with regard to pH changes and/or with regard to denaturing or oxidizing agents and/or with regard to proteolytic breakdown and/or with regard to a change in redox conditions.

Within the context of the invention, cleaning performance is to be understood as the lightening performance on one or more stains, in particular on laundry or dishes. Within the context of the invention both the washing, or cleaning agent encompassing the protease or the washing or cleaning liquor formed by this agent and the protease itself have a cleaning performance in their own right. The cleaning performance of the enzyme thus contributes to the cleaning performance of the agent or of the washing or cleaning liquor formed by the agent. The cleaning performance is preferably determined in the manner described further below.

A protease according to the invention has a proteolytic activity, which means that it is capable of hydrolyzing peptide bonds of a polypeptide or protein, in particular in a washing or cleaning agent. A protease according to the invention is therefore an enzyme that catalyzes the hydrolysis of peptide bonds and is thus capable of cleaving peptides or proteins. A protease according to the invention is moreover advantageously a mature protease, in other words the catalytically active molecule without signal peptides and/or propeptides. Unless otherwise indicated, the specified sequences also relate to mature enzymes.

In a further embodiment of the invention the protease encompasses an amino acid sequence which over the entire length thereof is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99% and 99.25% identical to the amino acid sequence specified in SEQ ID NO. 1 and which, in the listing according to SEQ ID NO. 1, has the amino acid substitution I21V in combination with at least one further amino acid substitution, the further amino acid substitution being selected from the group consisting of Q12L, M122L, N177V, A222S, V228I and T247N Particularly preferred proteases according to the invention are:
A protease encompassing an amino acid sequence which over the entire length thereof is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98% and 98.5% identical to the amino acid sequence specified in SEQ ID NO. 1 and which, in the listing according to SEQ ID NO. 1, has the amino acid substitution I21V in combination with the amino acid substitutions M122L, A222S and T247N.
A protease encompassing an amino acid sequence which over the entire length thereof is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence specified in SEQ ID NO. 1 and which, in the listing according to SEQ ID NO. 1, has the amino acid substitution I21V in combination with the amino acid substitutions N177V and V228I.

A protease encompassing an amino acid sequence which over the entire length thereof is at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98% and 98.5% identical to the amino acid sequence specified in SEQ ID NO. 1 and which, in the listing according to SEQ ID NO. 1, has the amino acid substitution I21V in combination with the amino acid substitutions Q12L, M122L and A222S.

A protease encompassing an amino acid sequence according to SEQ ID NO. 1 with the amino acid substitutions I21V, M122L, A222S and T247N in the listing according to SEQ ID NO. 1, in particular a protease according to SEQ ID NO. 4.

A protease encompassing an amino acid sequence according to SEQ ID NO. 1 with the amino acid substitutions I21V, N177V and V228I in the listing according to SEQ ID NO. 1, in particular a protease according to SEQ ID NO. 5.

A protease encompassing an amino acid sequence according to SEQ ID NO. 1 with the amino acid substitutions Q12L, I21V, M122L and A222S in the listing according to SEQ ID NO. 1, in particular a protease according to SEQ ID NO. 6.

Surprisingly it has moreover been established that further alternative possibilities are available for modifying the amino acid present at position 21 so as to obtain a performance improvement in the resulting protease. What is of fundamental importance is that the protease is modified at these positions in comparison to SEQ ID NO. 1, i.e. the amino acid present at this position is replaced by another proteinogenic amino acid, in other words by alanine or arginine or asparagine or aspartic acid or cysteine or glutamine or glutamic acid or glycine or histidine or leucine or lysine or methionine or phenylalanine or proline or serine or threonine or tryptophan or tyrosine or in particular valine. Since valine is particularly advantageous at this position, of the above amino acids conservative amino acids are preferred for valine, in other words those which, if valine is replaced by such an amino acid, do not lead to a change in polarity or charge, in particular glycine, alanine, isoleucine, leucine and methionine.

The identity of nucleic acid or amino acid sequences is determined by means of a sequence comparison. This sequence comparison is based on the conventionally used BLAST algorithm, which is established in the prior art (cf. for example Altschul, S. F., Gish, W., Miller, W., Myers, E. W. & Lipman, D. J. (1990) "Basic local alignment search tool", J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, p. 3389-3402) and which takes place in principle by assigning similar sequences of nucleotides or amino acids in the nucleic acid or amino acid sequences to one another. A tabular assignment of the relevant positions is known as an alignment. Another algorithm that is available in the prior art is the FASTA algorithm. Sequence comparisons (alignments), in particular multiple sequence comparisons, are created with computer programs. For example, the Clustal series (cf. for example Chenna et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217) or programs based on these programs or algorithms are frequently used. In the present patent application all sequence comparisons (alignments) were created with the Vector NTI® Suite 10.3 computer program (Invitrogen Corporation, 1600 Faraday Avenue, Carlsbad, Calif., USA) with the predefined default parameters, in which the AlignX module for sequence comparisons is based on ClustalW.

Such a comparison also allows an assertion to be made on the similarity to one another of the compared sequences. This is conventionally stated as the percentage identity, in other words the proportion of identical nucleotides or amino acid residues at the same positions or at positions corresponding to one another in an alignment. In amino acid sequences the broader concept of homology also includes conserved amino acid exchanges, in other words amino acids with a similar chemical activity, as these usually perform similar chemical activities within the protein. Therefore the similarity of the compared sequences can also be stated as the percentage homology or percentage similarity. Identity and/or homology data can refer to entire polypeptides or genes or only to individual regions. Homologous or identical regions of different nucleic acid or amino acid sequences are therefore defined by matches in the sequences. Such regions often have identical functions. They may be small and encompass only a few nucleotides or amino acids. Such small regions often perform essential functions for the overall activity of the protein. It can therefore be useful to relate sequence matches only to individual, possibly small regions. Unless otherwise specified, however, identity or homology data in the present application refers to the total length of the specified nucleic acid or amino acid sequence.

In a further embodiment of the invention the protease has the characterizing feature that its cleaning performance at least corresponds to that of a protease encompassing an amino acid sequence which corresponds to the amino acid sequence specified in SEQ ID NO. 1 and/or corresponds to at least that of a protease encompassing an amino acid sequence which corresponds to the amino acid specified in SEQ ID NO. 2 and/or corresponds to at least that of a protease according to SEQ ID NO. 3, the cleaning performance being determined in a washing system which contains a washing agent in a dose of between 4.5 and 7.0 grams per liter of washing liquor together with the protease, wherein the proteases to be compared are used in equal activities and the cleaning performance is determined with regard to an egg stain on cotton, in particular with regard to the stain whole egg/pigment on cotton: product no. C-S-37 obtainable from CFT (Center For Testmaterials) B.V., Vlaardingen, Netherlands by measuring the whiteness of the washed textiles, the washing process takes place for at least 30 minutes, optionally for 60 minutes, at a temperature of 20° C., and the water has a water hardness of between 15.5 and 16.5° (German hardness).

A preferred liquid washing agent for such a washing system has the following composition (all figures in percentage by weight): 0.3-0.5% xanthan gum, 0.2-0.4% antifoaming agent, 6-7% glycerol, 0.3-0.5% ethanol, 4-7% FAEOS (fatty alcohol ether sulfate), 24-28% non-ionic surfactants, 1% boric acid, 1-2% sodium citrate (dihydrate), 2-4% sodium carbonate, 14-16% coconut fatty acids, 0.5% HEDP (1-hydroxyethane-(1,1-diphosphonic acid)), 0-0.4% PVP (polyvinylpyrrolidone), 0-0.05% optical brightener, 0-0.001% dye, remainder demineralized water. The dose of liquid washing agent is preferably between 4.5 and 6.0 grams per liter of washing liquor, for example 4.7, 4.9 or 5.9 grams per liter of washing liquor. Washing preferably takes place in a pH range of between pH 8 and pH 10.5, preferably between pH 8 and pH 9.

A preferred powdered washing agent for such a washing system has the following composition (all figures in percentage by weight): 10% linear alkylbenzene sulfonate (sodium salt), 1.5% C12-C18 fatty alcohol sulfate (sodium salt), 2.0% C12-C18 fatty alcohol with 7 EO, 20% sodium carbonate, 6.5% sodium hydrogen carbonate, 4.0% amorphous sodium disilicate, 17% sodium carbonate peroxohydrate, 4.0% TAED, 3.0% polyacrylate, 1.0% carboxymethylcellulose, 1.0% phosphonate, 27% sodium sulfate, remainder: foam inhibitors, optical brightener, fragrances. The dose of powdered washing agent is preferably between 4.5 and 7.0 grams per liter of washing liquor, for example and particularly preferably 4.7 grams per liter of washing liquor, or 5.5, 5.9 or 6.7 grams per liter of washing liquor. Washing preferably takes place in a pH range of between pH 9 and pH 11.

Within the context of the invention the cleaning performance is determined at 20° C. using a solid washing agent as specified above, the washing process preferably lasting for 60 minutes.

The whiteness, i.e. the lightening of the stains, as a measure of cleaning performance is preferably determined by optical measuring methods, preferably by photometry. A suitable instrument for this purpose is the Minolta CM508d spectrometer, for example. The instruments used for the measurement are conventionally calibrated in advance with a white standard, preferably a white standard supplied with the instrument.

The use of proteases of equal activity ensures that even if there is any divergence in the ratio of active substance to total protein (the values of the specific activity), the actual enzymatic properties, in other words the cleaning performance on specific stains for example, are compared. Generally speaking, a low specific activity can be compensated for by adding a larger amount of protein. Methods of determining protease activity are familiar to the person skilled in the art in the field of enzyme technology and are routinely used by him. Such methods are disclosed for example in Tenside, volume 7 (1970), p. 125-132. Alternatively, the protease activity can be determined from the release of the chromophore para-nitroaniline (pNA) from the substrate suc-L-Ala-L-Ala-L-Pro-L-Phe-p-nitroanilide (AAPF). The protease cleaves the substrate and releases pNA. The release of pNA gives rise to an increase in extinction at 410 nm, the time course of which is a measure of enzymatic activity (cf. Del Mar et al., 1979). The measurement takes place at a temperature of 25° C., at pH 8.6 and at a wavelength of 410 nm. The measurement time is 5 min and the measuring interval 20 s to 60 s.

The protein concentration can be determined using known methods, for example the BCA method (bicinchoninic acid; 2,2'-biquinolyl-4,4'-dicarboxylic acid) or the Biuret method (A. G. Gornall, C. S. Bardawill and M. M. David, J. Biol. Chem., 177 (1948), p. 751-766). The active protein concentration can be determined in this regard by titrating the active centers using a suitable irreversible inhibitor (for proteases for example phenylmethylsulfonyl fluoride (PMSF)) and determining the residual activity (cf. M. Bender et al., J. Am. Chem. Soc. 88, 24 (1966), p. 5890-5913).

The protease activity is conventionally stated in protease units (PE). Suitable protease activities are for example 2.25, 5 or 10 PE per ml of washing liquor. The protease activity does not equal zero, however.

Proteins can be collected into groups of immunologically related proteins by means of the reaction with an antiserum or a particular antibody. The members of such a group have the characterizing feature that they have the same antigenic determinant, detected by an antibody. They are therefore structurally so similar to one another that they are detected by an antiserum or by particular antibodies. The invention therefore also provides proteases that have the characterizing feature that they have at least one and increasingly preferably two, three or four antigenic determinants that match a protease according to the invention. By virtue of their immunological matches, such proteases are structurally so similar to the proteases according to the invention that they can also be assumed to have the same function.

In addition to the amino acid modifications described above, proteases according to the invention can have further amino acid modifications, in particular amino acid substitutions, insertions or deletions. Such proteases are developed further by means of selective genetic modification, for example, i.e. by means of mutagenesis techniques, and are optimized for certain applications or with regard to specific properties (e.g. with regard to their catalytic activity, stability, etc.). Furthermore, nucleic acids according to the invention can be introduced into recombination formulations and then used to create entirely new proteases or other polypeptides.

The objective is to introduce selective mutations such as substitutions, insertions or deletions into the known molecules so as to improve the cleaning performance for example of enzymes according to the invention. To this end the surface charges and/or the isoelectric point of the molecules, and hence their interactions with the substrate, can be modified in particular. Thus, for example, the net charge of the enzymes can be modified so as to influence substrate binding, in particular for use in washing and cleaning agents. Alternatively or in addition, the stability of the protease can be increased by means of one or more appropriate mutations, thus improving the cleaning performance of the protease. Advantageous properties of individual mutations, e.g. individual substitutions, can complement one another. Thus within the context of the invention a protease that has already been optimized with regard to certain properties, for example in terms of its stability in respect of surfactants and/or bleaching agents and/or other components, can also be developed further.

The following convention is used to describe substitutions that relate to just one amino acid position (amino acid exchanges): first of all the naturally occurring amino acid is identified in the form of the internationally accepted one-letter code; this is followed by the associated sequence position and finally the inserted amino acid. Multiple exchanges within the same polypeptide chain are separated from one another by means of slashes. In the case of insertions, additional amino acids are listed after the sequence position. In the case of deletions the missing amino acid is replaced by a symbol such as an asterisk or a dash. For example, A95G describes the substitution of alanine at position 95 with glycine, A95AG the insertion of glycine after the amino acid alanine at position 95 and A95* the deletion of alanine at position 95. This nomenclature is familiar to the person skilled in the art in the field of enzyme technology.

The invention therefore also provides a protease with the characterizing feature that it is obtainable from a protease as described above as the starting molecule by single or multiple conservative amino acid substitution, said protease, in the listing according to SEQ ID NO. 1, still having the amino acid substitution I21V according to the invention in combination with at least one further amino acid substitution, the further amino acid substitution being selected from the group consisting of Q12L, M122L, N177V, A222S, V228I and T247N, as described above. The term "conservative amino acid substitution" denotes the exchange (substitution) of one amino acid residue for another amino acid residue, wherein this exchange does not lead to a change in the polarity or charge at the position of the exchanged amino acid, for example the exchange of one non-polar amino acid residue for another non-polar amino acid residue. Conservative amino acid substitutions within the context of the invention encompass for example G=A=S, I=V=L=M, D=E, N=Q, K=R, Y=F, S=T, G=A=I=V=L=M=Y=F=W=P=S=T.

Alternatively or in addition, the protease has the characterizing feature that it is obtainable from a protease according to the invention as the starting molecule by fragmentation or by deletion, insertion or substitution mutagenesis and encompasses an amino acid sequence that over a length of at least 50, 60, 70, 80, 90, 100, 110, 120, 130, 140, 150, 160, 170, 180, 190, 200, 210, 220, 230, 240, 250, 260, 265, 266 or 267 successive amino acids matches the starting molecule, the amino acid substitution I21V according to the invention contained in the starting molecule still being present in combination with at least one further amino acid substitution, said further amino acid substitution being selected from the group consisting of Q12L, M122L, N177V, A222S, V228I and T247N, as described above.

Thus, for example, it is possible to delete individual amino acids at the termini or in the loops of the enzyme without proteolytic activity being lost or reduced as a consequence. Moreover, the allergenicity for example of relevant enzymes can also be reduced by means of such fragmentation or deletion, insertion or substitution mutagenesis, thus improving their overall usability. The enzymes advantageously retain their proteolytic activity even after mutagenesis, i.e. their proteolytic activity at least corresponds to that of the starting enzyme. Substitutions can also have advantageous effects. Both individual and multiple successive amino acids can be exchanged for other amino acids.

Alternatively or in addition, the protease has the characterizing feature that it is obtainable from a protease according to the invention as the starting molecule by one or more amino acid substitutions in positions which are assigned to positions 3, 4, 36, 42, 47, 56, 61, 69, 87, 96, 99, 101, 102, 104, 114, 118, 120, 130, 139, 141, 142, 154, 157, 188, 193, 199, 205, 211, 224, 229, 236, 237, 242, 243, 255 and 268 of the protease from Bacillus lentus according to SEQ ID NO. 3 in an alignment, said protease, in the listing according to SEQ ID NO. 1, still having the amino acid substitution I21V according to the invention in combination with at least one further amino acid substitution, the further amino acid substitution being selected from the group consisting of Q12L, M122L, N177V, A222S, V228I and T247N, as described above. The further amino acid positions are defined by aligning the amino acid sequence of a protease according to the invention with the amino acid sequence of the protease from Bacillus lentus, as specified in SEQ ID NO. 3. Such an alignment is shown in FIG. 1. As the protease from Bacillus lentus is an important reference molecule in the prior art for describing novel proteases and amino acid modifications, and the novel proteases described here and thus also the sequence thereof were hitherto unknown, it is advantageous to refer to the protease from Bacillus lentus (SEQ ID NO. 3) in the assignment of amino acid positions. Furthermore, the assignment of positions is based on the mature protein. This assignment should also be used in particular if the amino acid sequence of a protease according to the invention encompasses a higher number of amino acid residues than the protease from Bacillus lentus according to SEQ ID NO. 3. Starting from the specified positions in the amino acid sequence of the protease from Bacillus lentus, the modification positions in a protease according to the invention are those assigned to precisely those positions in an alignment, according to FIG. 1 for example.

Advantageous positions for sequence modifications, in particular substitutions, of the protease from Bacillus lentus which are preferably of importance when transferred to homologous positions of the proteases according to the invention and impart advantageous functional properties to the protease are accordingly positions 3, 4, 36, 42, 47, 56, 61, 69, 87, 96, 99, 101, 102, 104, 114, 118, 120, 130, 139, 141, 142, 154, 157, 188, 193, 199, 205, 211, 224, 229, 236, 237, 242, 243, 255 and 268, for assignment in an alignment with SEQ ID NO. 3 and hence in the listing according to SEQ ID NO. 3. In the specified positions the following amino acid residues are present in the wild-type molecule of the protease from Bacillus lentus: S3, V4, S36, N42, A47, T56, G61, T69, E87, A96, R99, A101, I102, S104, N114, H118, A120, S130, S139, T141, S142, S154, S157, A188, V193, V199, G205, L211, A224, K229, S236, N237, N242, H243, N255 and T268.

In particular, substitutions 3T, 4I, 61A, 99G, 99A, 99S, 99E, 154D, 154E, 211D, 211G and 211E for example are advantageous, unless the corresponding homologous positions in a protease according to the invention are already naturally occupied by one of these preferred amino acids. The exchanges 3T and 4I have a stabilizing effect on the molecule that leads to an improvement in the cleaning performance of the protease and hence to an improved cleaning performance of a washing or cleaning agent containing this protease.

Further confirmation of the correct assignment of the amino acids to be modified, i.e. in particular of their functional equivalence, can be provided by comparative experiments in which the two positions assigned to one another on the basis of an alignment are modified in the same way in the two proteases being compared, and observations are undertaken to determine whether the enzymatic activity is modified in the same way in both cases. If for example an amino acid exchange at a particular position of the protease from Bacillus lentus according to SEQ ID NO. 3 is accompanied by a change in an enzyme parameter, for example by an increase in the $K_M$ value, and if a corresponding change in the enzyme parameter, thus for example likewise an increase in the $K_M$ value, is observed in a protease variant according to the invention whose amino acid exchange was achieved through the same inserted amino acid, this can be regarded as a confirmation of the correct assignment.

All specified elements can also be applied to the methods according to the invention for producing a protease. Thus a method according to the invention further encompasses one or more of the following process steps:

(a) Introducing a single or multiple conservative amino acid substitution, wherein the protease, in the listing according to SEQ ID NO. 1, has the amino acid substitution I21V in combination with at least one further amino acid substitution, the further amino acid substitution being selected from the group consisting of Q12L, M122L, N177V, A222S, V228I and T247N;

(b) Modifying the amino acid sequence by fragmentation or by deletion, insertion or substitution mutagenesis such that the protease encompasses an amino acid sequence which over a length of at least 50, 60, 70, 80, 90, 100, 110, 120, 130, 140, 150, 160, 170, 180, 190, 200, 210, 220, 230, 240, 250, 260, 265, 266 or 267 successive amino acids matches the starting molecule, wherein the amino acid substitution I21V contained in the starting molecule is still present in combination with at least one further amino acid substitution, the further amino acid substitution being selected from the group consisting of Q12L, M122L, N177V, A222S, V228I and T247N;

(c) Introducing a single or multiple amino acid substitution into one or more of the positions which are assigned to positions 3, 4, 36, 42, 47, 56, 61, 69, 87, 96, 99, 101, 102, 104, 114, 118, 120, 130, 139, 141, 142, 154, 157, 188, 193, 199, 205, 211, 224, 229, 236, 237, 242, 243, 255 and 268 of the protease from *Bacillus lentus* according to SEQ ID NO. 3 in an alignment, said protease, in the listing according to SEQ ID NO. 1, having the amino acid substitution I21V in combination with at least one further amino acid substitution, the further amino acid substitution being selected from the group consisting of Q12L, M122L, N177V, A222S, V228I and T247N.

All references also apply to the methods according to the invention.

In further embodiments of the invention the protease or the protease produced by a method according to the invention is still at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99% or 99.25% identical to the amino acid sequence specified in SEQ ID NO. 1 over the entire length thereof. The protease or the protease produced by a method according to the invention has the amino acid substitution I21V in combination with at least one further amino acid substitution, the further amino acid substitution being selected from the group consisting of Q12L, M122L, N177V, A222S, V228I and T247N.

The invention also provides a protease as described above which is additionally stabilized, in particular by means of one or more mutations, for example substitutions, or by coupling to a polymer. Increasing the stability in storage and/or during use, for example during the washing process, leads to a longer retention of the enzymatic activity and hence to an improvement in the cleaning performance. All stabilization possibilities that are convenient and/or are described in the prior art are suitable in principle. Stabilizations achieved by means of mutations of the enzyme itself are preferred, since such stabilizations require no further process steps once the enzyme has been obtained. Examples of sequence modifications that are suitable for this purpose are given above. Further suitable sequence modifications are known from the prior art. Thus proteases can also be stabilized by exchanging one or more tyrosine residues for other amino acids, for example.

All references also apply to the methods according to the invention.

In further embodiments of the invention the protease or the protease produced by a method according to the invention is still at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99% or 99.25% identical to the amino acid sequence specified in SEQ ID NO. 1 over the entire length thereof. The protease or the protease produced by a method according to the invention has the amino acid substitution I21V in combination with at least one further amino acid substitution, the further amino acid substitution being selected from the group consisting of Q12L, M122L, N177V, A222S, V228I and T247N.

The invention also provides a protease as described above which is additionally stabilized, in particular by means of one or more mutations, for example substitutions, or by coupling to a polymer. Increasing the stability in storage and/or during use, for example during the washing process, leads to a longer retention of the enzymatic activity and hence to an improvement in the cleaning performance. All stabilization possibilities that are convenient and/or are described in the prior art are suitable in principle. Stabilizations achieved by means of mutations of the enzyme itself are preferred, since such stabilizations require no further process steps once the enzyme has been obtained. Examples of sequence modifications that are suitable for this purpose are given above. Further suitable sequence modifications are known from the prior art. Thus proteases can also be stabilized by exchanging one or more tyrosine residues for other amino acids, for example.

Further possibilities for stabilization include, for example:
Modifying the binding of metal ions, in particular of calcium binding sites, for example by exchanging one or more of the amino acids involved in calcium binding for one or more negatively charged amino acids and/or by introducing sequence modifications in at least one of the sequences of the two amino acids arginine and glycine;
Protecting against the influence of denaturing agents such as surfactants by means of mutations that bring about a change in the amino acid sequence on or at the surface of the protein;
Exchanging amino acids located close to the N-terminus for those that are assumed to come into contact with the rest of the molecule by means of non-covalent interactions and thus contribute to maintaining the global structure.

Preferred embodiments are those in which the enzyme is stabilized in a plurality of ways, since a plurality of stabilizing mutations have a cumulative or synergistic effect.

The invention also provides a protease as described above with the characterizing feature that it has at least one chemical modification. A protease having such a modification is described as a derivative, i.e. the protease is derivatized.

Within the meaning of the present application derivatives are thus understood to be proteins whose pure amino acid chain has been chemically modified. Such derivatizations can take place in vivo, for example, through the host cell that expresses the protein. Couplings of low-molecular-weight compounds such as lipids or oligosaccharides are of particular importance in this respect. Derivatizations can also be performed in vitro, however, for instance through the chemical conversion of a side chain of an amino acid or through covalent bonding of another compound to the protein. The coupling of amines to carboxyl groups of an enzyme to change the isoelectric point is possible, for example. Such another compound can also be another protein, which is bound to a protein according to the invention by means of bifunctional chemical compounds, for example. Derivatization can likewise be understood to be the covalent bonding to a macromolecular carrier or a non-covalent inclusion in suitable macromolecular cage structures. Derivatizations can influence the substrate specificity or bonding strength on the substrate, for example, or can give rise to a temporary blocking of enzymatic activity if the coupled substance is an inhibitor. This can be useful for the period of storage, for example. Such modifications can moreover influence stability or enzymatic activity. They can moreover also serve to reduce the allergenicity and/or immunogenicity of the protein and thus increase its skin compatibility, for example. Couplings with for example macromolecular compounds, for example polyethylene glycol, can improve the protein with regard to stability and/or skin compatibility.

In the broadest sense derivatives of a protein according to the invention can also be understood to be preparations of these proteins. Depending on the manner in which it is obtained, recovered or prepared, a protein can be associated with various other substances, for example from the culture of the producing microorganisms. Other substances can also be deliberately added to a protein, to increase its stability in storage for example. All preparations of a protein according to the invention are therefore also inventive. This is irrespective of whether or not this enzymatic activity actually develops in a particular preparation. It can be desirable for it to have little or no activity during storage and for its enzymatic function to develop only at the moment of use. This can be controlled by means of appropriate accompanying substances, for example. In particular, the joint preparation of proteases with protease inhibitors is possible in this regard.

With regard to all proteases or protease variants and/or derivatives described above, in the context of the present invention those whose activity at least corresponds to that of the protease according to SEQ ID NO. 1 and/or SEQ ID NO. 2 and/or SEQ ID NO. 3 and/or whose cleaning performance at least corresponds to that of the protease according to SEQ ID NO. 1 and/or SEQ ID NO. 2 and/or SEQ ID NO. 3 are particularly preferred, the cleaning performance being determined in a washing system as described above.

The invention also provides a nucleic acid that codes for a protease according to the invention along with a vector containing such a nucleic acid, in particular a cloning vector or an expression vector.

These can be DNA or RNA molecules. They can be present as a single strand, as a complementary single strand to this single strand, or as a double strand. In the case of DNA molecules in particular, the sequences of both complementary strands must be taken into consideration in all three possible reading frames. It must also be borne in mind that different codons, i.e. base triplets, can code for the same amino acids, such that a particular amino acid sequence can be encoded by several different nucleic acids. Owing to this degeneracy of the genetic code, all nucleic acid sequences which can code for one of the aforementioned proteases are included in this subject matter of the invention. The person skilled in the art is able to determine these nucleic acid sequences with absolute certainty, since despite the degeneracy of the genetic code, defined amino acids can be assigned to individual codons. Thus, starting from an amino acid sequence, the person skilled in the art can easily determine the nucleic acids that code for this amino acid sequence. Furthermore, in the case of nucleic acids according to the invention one or more codons can be replaced by synonymous codons. This aspect relates in particular to the heterologous expression of the enzymes according to the invention. Thus every organism, for example a host cell of a production strain, has a particular codon usage. Codon usage is understood to be the translation of the genetic code in amino acids by the individual organism. Bottlenecks can occur in protein biosynthesis if the codons on the nucleic acid are balanced by a comparatively low number of charged tRNA molecules in the organism. Although coding for the same amino acid, this results in a codon being translated less efficiently in the organism than a synonymous codon that codes for the same amino acid. Owing to the presence of a higher number of tRNA molecules for the synonymous codon, it can be translated more efficiently in the organism.

Using methods that are in common in the field, such as for example chemical synthesis or polymerase chain reaction (PCR) in conjunction with standard methods of molecular biology and/or protein chemistry, a person skilled in the art can use known DNA and/or amino acid sequences to produce the corresponding nucleic acids through to complete genes. Such methods are known for example from Sambrook, J., Fritsch, E. F. and Maniatis, T. 2001. Molecular cloning: a laboratory manual, 3rd Edition, Cold Spring Harbor Laboratory Press.

Within the meaning of the present invention vectors are understood to be elements consisting of nucleic acids which contain a nucleic acid according to the invention as the characterizing nucleic acid region. They are able to establish this nucleic acid in a species or a cell line across a number of generations or cell divisions as a stable genetic element. When used in bacteria in particular, vectors are specific plasmids, in other words circular genetic elements. In the context of the present invention, a nucleic acid according to the invention is cloned into a vector. Vectors include for example those originating from bacterial plasmids, viruses or bacteriophages or predominantly synthetic vectors or plasmids having elements of diverse origin. With the other genetic elements that are present, vectors are able to establish themselves in the corresponding host cells over a number of generations as stable units. They can exist extrachromosomally as separate units or integrate into a chromosome or chromosomal DNA.

Expression vectors encompass nucleic acid sequences which enable them to replicate within the host cells that contain them, preferably microorganisms, particularly preferably bacteria, and there to express a nucleic acid that is contained within them. Expression is influenced in particular by the promoter(s) that regulate transcription. Expression can be carried out in principle by the natural promoter originally located ahead of the nucleic acid that is to be expressed or by a host cell promoter provided on the expression vector or alternatively by a modified or completely different promoter of another organism or another host cell. In the present case at least one promoter is provided for the expression of a nucleic acid according to the invention and used for the expression thereof. Expression vectors can moreover be regulable, for example by altering the cultivation conditions or by achieving a particular cell density of the host cells containing them or by adding certain substances, in particular activators of gene expression. One example of such a substance is the galactose derivative isopropyl β-D-thiogalactopyranoside (IPTG), which is used as an activator of the bacterial lactose operon (lac operon). In contrast to expression vectors, the nucleic acid contained in cloning vectors is not expressed.

The invention also provides a non-human host cell containing a nucleic acid according to the invention or a vector according to the invention or containing a protease according to the invention, in particular a non-human host cell that secretes the protease into the medium surrounding the host cell. A nucleic acid according to the invention or a vector according to the invention is preferably transformed into a microorganism which then constitutes a host cell according to the invention. Alternatively, individual components, i.e. nucleic acid components or fragments of a nucleic acid according to the invention can be introduced into a host cell in such a way that the resulting host cell then contains a nucleic acid according to the invention or a vector according to the invention. This procedure is particularly suitable if the host cell already contains one or more constituents of a nucleic acid according to the invention or of a vector according to the invention and the further constituents can then be added accordingly. Methods of cell transformation are established in the prior art and are sufficiently known to the person skilled in the art. All cells, in other words prokaryotic or eukaryotic cells, are suitable in principle as host cells. Host cells that allow advantageous genetic handling, in terms for example of transformation with the nucleic acid or the vector and the stable establishing thereof, are preferred, for example singlecelled fungi or bacteria. Preferred host cells also offer good microbiological and biotechnological handling ability. This relates for example to ease of cultivation, high growth rates, low requirements as regards fermentation media and good production and secretion rates for foreign proteins. Preferred host cells according to the invention secrete the (transgenically) expressed protein into the medium surrounding the host cells. The proteases can moreover be modified after production by the cells that produced them, for example by the attachment of sugar molecules, by formulations, aminations, etc. Such post-translational modifications may influence the protease function.

Further preferred embodiments are host cells whose activity can be regulated because of genetic regulatory elements, which are provided on the vector, for example, or which can also be present from the outset in these cells. The host cells can be stimulated to expression by for example the controlled addition of chemical compounds serving as activators, by changing the cultivation conditions or on reaching a defined cell density. This allows an economic production of the proteins according to the invention. An example of such a compound is IPTG, as described above.

Preferred host cells are prokaryotic or bacterial cells. Bacteria have the characterizing feature of short generation times and low demands as regards cultivation conditions. Cost-effective cultivation methods or production methods can be established in this way. Furthermore, the person skilled in the art has a wealth of experience regarding bacteria in fermentation technology. For a wide variety of reasons, which must be determined by experiment in individual cases, including nutrient sources, rate of product formation, time constraints, etc., gram-negative or gram-positive bacteria may be suitable for a specific production.

In the case of gram-negative bacteria such as for example *Escherichia coli*, a large number of proteins are secreted into the periplasmic space, in other words into the compartment between the two membranes bounding the cells. This can be advantageous for specific applications. Furthermore, gram-negative bacteria can be developed so that they secrete the expressed proteins not only into the periplasmic space but also into the medium surrounding the bacterium. By contrast, gram-positive bacteria such as for example *Bacilli* or *Actinomycetes* or other representatives of the Actinomycetales have no external membrane, so secreted proteins are released directly into the medium surrounding the bacteria, generally the nutrient medium, from which the expressed proteins can be purified. They can be isolated directly from the medium or processed further. In addition, gram-positive bacteria are related to or identical to most source organisms for technically important enzymes and they usually themselves form comparable enzymes, such that they have a similar codon usage and their protein synthesis apparatus is naturally aligned accordingly.

Host cells according to the invention can be modified in terms of their requirements as regards culture conditions, can have other or additional selection markers or can also express other or additional proteins. They can also in particular be host cells that express a plurality of proteins or enzymes transgenically.

The present invention is applicable in principle to all microorganisms, in particular to all fermentable microorganisms, particularly preferably to those of the *Bacillus* genus, and leads through the use of such microorganisms to the production of proteins according to the invention. Such microorganisms then constitute host cells within the meaning of the invention.

In a further embodiment of the invention the host cell has the characterizing feature that it is a bacterium, preferably one that is selected from the group of genera comprising *Escherichia, Klebsiella, Bacillus, Staphylococcus, Corynebacterium, Arthrobacter, Streptomyces, Stenotrophomonas* and *Pseudomonas*, more preferably one that is selected from the group comprising *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacterium glutamicum, Arthrobacter oxidans, Streptomyces lividans, Streptomyces coelicolor* and *Stenotrophomonas maltophilia*.

The host cell can however also be a eukaryotic cell, which has the characterizing feature of having a cell nucleus. The invention therefore also provides a host cell having the characterizing feature of having a cell nucleus. Unlike prokaryotic cells, eukaryotic cells are capable of the posttranslational modification of the protein that is formed. Examples thereof are fungi such as Actinomycetene or yeasts such as *Saccharomyces* or *Kluyveromyces*. This property can be particularly advantageous, for example, if in connection with their synthesis the proteins are to undergo specific modifications that such systems allow. The modifications that eukaryotic systems perform, in conjunction with protein synthesis in particular, include for example the binding of low-molecular-weight compounds such as membrane anchors or oligosaccharides. Such oligosaccharide modifications can be desirable as a means of lowering the allergenicity of an expressed protein, for example. A coexpression with the enzymes that are naturally formed by such cells, such as cellulases or lipases for example, can also be advantageous. Furthermore, thermophilic fungal expression systems for example can be particularly suitable for the expression of temperature-resistant proteins or variants.

The host cells according to the invention are cultivated and fermented in the conventional way, in discontinuous or continuous systems for example. In the first case a suitable nutrient medium is inoculated with the host cells and the product is harvested from the medium after a time that is to be determined by experiment. Continuous fermentations have the characterizing feature of achieving a dynamic equilibrium in which over a comparatively long period some cells die but also regenerate and the protein that is formed can be removed from the medium at the same time.

Host cells according to the invention are preferably used to produce proteases according to the invention. The invention therefore also provides a method for producing a protease, encompassing
a) cultivating a host cell according to the invention
b) isolating the protease from the culture medium or from the host cell.

This subject matter of the invention preferably encompasses fermentation methods. Fermentation methods are known per se from the prior art and constitute the actual large-scale production step, which is generally followed by a suitable purification method for the product obtained, for example the protease according to the invention. All fermentation methods that are based on a corresponding method for producing a protease according to the invention constitute embodiments of this subject matter of the invention.

Fermentation methods having the characterizing feature that the fermentation is performed by means of a feed strategy are suitable in particular. Here the media constituents that are consumed by the continuing cultivation are fed in. Considerable increases in both cell density and cell mass or dry mass and/or above all in the activity of the protease in question can be achieved in this way. The fermentation can moreover also be designed in such a way that undesired metabolites are filtered out or are neutralized by adding buffers or suitable counterions.

The protease that is produced can be harvested from the fermentation medium. Such a fermentation method is preferable to an isolation of the protease from the host cell, i.e. a product recovery from the cell mass (dry mass), but it requires the provision of suitable host cells or of one or more suitable secretion markers or mechanisms and/or transport systems so that the host cells secrete the protease into the fermentation medium. Without secretion the protein can alternatively be isolated from the host cell, i.e. purified from the cell mass, for example by precipitation with ammonium sulfate or ethanol, or by chromatographic purification.

All aforementioned elements can also be combined into methods for producing proteases according to the invention.

The invention also provides an agent having the characterizing feature that it contains a protease according to the invention as described above. The agent is preferably a washing or cleaning agent. Since proteases according to the invention exhibit advantageous cleaning performances, in particular on egg-containing stains, the agents are suitable and advantageous for the removal of such stains in particular.

This subject matter of the invention includes all conceivable types of washing and cleaning agents, both concentrates and agents intended for use in undiluted form, for use on a commercial scale, in washing machines or for hand washing or cleaning. They include for example washing agents for textiles, carpets or natural fibers for which the term washing agent is used. They also include for example dishwashing agents for automatic dishwashers or hand dishwashing agents or cleaners for hard surfaces such as metal, glass, porcelain, ceramics, tiles, stone, coated surfaces, plastics, wood or leather, for which the term cleaning agent is used, i.e. in addition to hand and automatic dishwashing agents for example also scouring agents, glass cleaners, toilet fresheners, etc. Within the context of the invention the washing and cleaning agents additionally include washing auxiliary agents that are added to the actual washing agent during the manual or automatic textile washing process to achieve an additional effect. Washing and cleaning agents within the context of the invention moreover also include textile pre- and aftertreatment agents, i.e. agents that are brought into contact with the laundry item before it is actually washed, for example to partially dissolve stubborn stains, and also agents that in a subsequent step after the actual textile washing process impart further desirable properties to the laundry item, such as a pleasant feel, crease resistance or low static charge. The latter agents include inter alia fabric softeners.

The washing or cleaning agents according to the invention, which can in particular be in the form of powdered solids, in consolidated particle form or in the form of homogeneous solutions or suspensions, can contain, in addition to a protease according to the invention, all known ingredients that are conventionally used in such agents, wherein at least one further ingredient is preferably present in the agent. The agents according to the invention can contain in particular surfactants, builders, peroxygen compounds or bleach activators. They can moreover contain water-miscible organic solvents, further enzymes, sequestering agents, electrolytes, pH regulators and/or further auxiliary substances such as optical brighteners, graying inhibitors, foam regulators and dyes and fragrances as well as combinations thereof.

A combination of a protease according to the invention and one or more further ingredients of the agent is advantageous in particular, since in preferred embodiments according to the invention such an agent exhibits an improved cleaning performance due to synergies that occur. Such a synergy can be achieved in particular through the combination of a protease according to the invention and a surfactant and/or a builder and/or a peroxygen compound and/or a bleach activator.

Advantageous ingredients of agents according to the invention are disclosed in the international patent application WO2009/121725, beginning on page 5, penultimate paragraph, and ending on page 13 after the second paragraph. Reference is expressly made to this disclosure, and the disclosure content therein is included in the present patent application.

An agent according to the invention advantageously contains the protease in an amount from 2 µg to 20 mg, preferably from 5 µg to 17.5 mg, particularly preferably from 20 µg to 15 mg and most particularly preferably from 50 µg to 10 mg per g of agent. The protease contained in the agent and/or further ingredients of the agent can moreover be encapsulated by a substance that is impermeable for the enzyme at room temperature or in the absence of water and becomes permeable for the enzyme under the application conditions of the agent. Such an embodiment of the invention thus has the characterizing feature that the protease is encapsulated by a substance that is impermeable for the protease at room temperature or in the absence of water. The washing or cleaning agent can furthermore itself be packed in a container, preferably an air-permeable container, from which it is released shortly before use or during the washing process.

In further embodiments of the invention the agent has the characterizing feature that it
(a) is in solid form, in particular as a free-flowing powder having a bulk density from 300 g/l to 1200 g/l, in particular 500 g/l to 900 g/l, or
(b) is in paste or in liquid form, and/or
(c) is present as a one-component system, or
(d) is divided into a plurality of components.

These embodiments of the present invention encompass all solid, powdered, liquid, gel or paste presentation forms of agents according to the invention, which can optionally also consist of a plurality of phases and be present in compressed or non-compressed form. The agent can take the form of a free-flowing powder, in particular having a bulk density from 300 g/l to 1200 g/l, in particular 500 g/l to 900 g/l or 600 g/l to 850 g/l. The solid presentation forms of the agent also include extrudates, granules, tablets or pouches. The agent can alternatively also be in liquid, gel or paste form, for example in the form of a non-aqueous liquid washing agent or a non-aqueous paste or in the form of an aqueous liquid washing agent or a water-containing paste. The agent can moreover take the form of a one-component system. Such agents consist of one phase. An agent can alternatively also consist of a plurality of phases. Such an agent is thus divided into a plurality of components.

Washing or cleaning agents according to the invention can exclusively contain a protease. Alternatively they can also contain further hydrolytic enzymes or other enzymes in an appropriate concentration for the effectiveness of the agent. Agents that additionally encompass one or more further enzymes thus constitute a further embodiment of the invention. All enzymes that can develop a catalytic activity in the agent according to the invention are preferably suitable for use as further enzymes, in particular a protease, amylase, cellulase, hemicellulase, mannanase, tannase, xylanase, xanthanase, xyloglucanase, β-glucosidase, pectinase, carrageenase, perhydrolase, oxidase, oxidoreductase or a lipase, and mixtures thereof. Further enzymes are advantageously each contained in the agent in an amount from $1\times10^{-8}$ to 5 wt. %, relative to active protein. Each further enzyme is increasingly preferably contained in agents according to the invention in an amount from $1\times10^{-7}$ to 3 wt. %, from 0.00001 to 1 wt. %, from 0.00005 to 0.5 wt. %, from 0.0001 to 0.1 wt. % and particularly preferably from 0.0001 to 0.05 wt. %, relative to active protein. The enzymes particularly preferably demonstrate synergistic cleaning performances in respect of specific stains or marks, in other words the enzymes contained in the agent composition are mutually supportive of one another in their cleaning performance. Such a synergy most particularly preferably exists between the protease included according to the invention and a further enzyme of an agent according to the invention, in particular between the cited protease and the amylase and/or a lipase and/or a mannanase and/or a cellulase and/or a pectinase. Synergistic effects can occur not only between different enzymes but also between one or more enzymes and other ingredients of the agent according to the invention.

The invention also provides a method for cleaning textiles or hard surfaces, having the characterizing feature that an agent according to the invention is used in at least one process step or wherein a protease according to the invention becomes catalytically active in at least one process step, in particular such that the protease is used in an amount from 40 µg to 4 g, preferably from 50 µg to 3 g, particularly preferably from 100 µg to 2 g and most particularly preferably from 200 µg to 1 g.

Such methods include both manual and automatic methods, automatic methods being preferred. Methods for cleaning textiles generally have the characterizing feature that in a plurality of process steps various active cleaning substances are applied to the item to be cleaned and washed off after the contact period or that the item to be cleaned is treated with a washing agent or a solution or dilution of that agent by some other means. The same applies to methods for cleaning all materials other than textiles, in particular hard surfaces. All conceivable washing or cleaning methods can be enhanced in at least one of the process steps by the use of a washing or cleaning agent according to the invention or of a protease according to the invention and then constitute embodiments of the present invention. All elements, subject matters and embodiments described for proteases according to the invention or for agents containing them can also be applied to this subject matter of the invention. Therefore reference is expressly made here to the disclosure at the corresponding point, with the note that this disclosure also applies to the above methods according to the invention.

Since proteases according to the invention naturally already have a hydrolytic activity and develop it even in media that otherwise have no cleaning power, such as in simple buffers for example, an individual and/or the only step of such a method can consist of bringing a protease according to the invention, optionally as the only active cleaning component, into contact with the stain, preferably in a buffer solution or in water. This constitutes a further embodiment of this subject matter of the invention.

Methods for the treatment of textile raw materials or for textile care in which a protease according to the invention becomes active in at least one process step also constitute alternative embodiments of this subject matter of the invention. Of such methods, those for textile raw materials, fibers or textiles containing natural constituents are preferred, most particularly for those containing wool or silk.

The invention also provides the use of an agent according to the invention for cleaning textiles or hard surfaces, or of a protease according to the invention for cleaning textiles or hard surfaces, in particular such that the protease is used in an amount from 40 µg to 4 g, preferably from 50 µg to 3 g, particularly preferably from 100 µg to 2 g and most particularly preferably from 200 µg to 1 g.

All elements, subject matters and embodiments described for proteases according to the invention or for agents containing them can also be applied to this subject matter of the invention. Therefore reference is expressly made here to the disclosure at the corresponding point, with the note that this disclosure also applies to the above use according to the invention.

EXAMPLES

All molecular biology procedures follow standard methods, such as are specified for example in the manual by Fritsch, Sambrook and Maniatis "Molecular cloning: a laboratory manual", Cold Spring Harbor Laboratory Press, New York, 1989, or comparable relevant works. Enzymes and kits were used in accordance with the manufacturer's instructions.

Example 1

Starting from a protease having an amino acid sequence according to SEQ ID NO. 1, a protease variant according to the invention was produced by site-directed mutagenesis in the nucleic acid that codes for the protease, by means of the SeSaM method (Wong, T. S. et al. (2004): Sequence saturation mutagenesis (SeSaM): a novel method for directed evolution. Nucleic Acids Res. 32, 26ff). The codons for the specified amino acid positions were modified so that an exchange of amino acids as specified took place relative to the amino acid sequence. The protease variant was expressed in the customary technical manner by transformation of Bacillus subtilis DB 104 (Kawamura and Doi (1984), J. Bacteriol., Vol. 160 (1), p. 442-444) with a corresponding expression vector and subsequent culture of the transformants expressing the protease variant. Protease variant 1: Protease having an amino acid sequence according to SEQ ID NO. 1 with the amino acid substitutions I21V, M122L, A222S and T247N in the listing according to SEQ ID NO. 1 (SEQ ID NO. 4);

Protease variant 2: Protease having an amino acid sequence according to SEQ ID NO. 1 with the amino acid substitutions I21V, N177V and V228I in the listing according to SEQ ID NO. 1 (SEQ ID NO. 5);

Protease variant 3: Protease having an amino acid sequence according to SEQ ID NO. 1 with the amino acid substitutions Q12L, I21V, M122L and A222S in the listing according to SEQ ID NO. 1 (SEQ ID NO. 6)

Example 2

Determining the Cleaning Performance when Used in a Commercial Powdered Washing Agent Standardized soiled textiles were used for this example. The following stain was used:
A: whole egg/pigment on cotton: product no. C-S-37 obtainable from CFT (Center For Testmaterials) B.V., Vlaardingen, Netherlands.

Various washing agent formulations were tested for their cleaning performance using this test material. To this end the batches were washed for 60 minutes at a temperature of 20° C. or 40° C. The dose was 4.7 g of washing agent per liter of washing liquor. Tap water with a water hardness of 16° German hardness was used for washing.

A washing agent base formulation of the following composition (all figures in percentage by weight) was used as the control washing agent: 10% linear alkylbenzene sulfonate (sodium salt), 1.5% C12-C18 fatty alcohol sulfate (sodium salt), 2.0% C12-C18 fatty alcohol with 7 EO, 20% sodium carbonate, 6.5% sodium hydrogen carbonate, 4.0% amorphous sodium disilicate, 17% sodium carbonate peroxohydrate, 4.0% TAED, 3.0% polyacrylate, 1.0% carboxymethylcellulose, 1.0% phosphonate, 27% sodium sulfate, remainder: foam inhibitors, optical brightener, fragrances.

The following proteases were added to the washing agent base formulation in equal activities (5 PE/ml final concentration) for the various experimental series: protease variant 1 (batch 1), protease variant 2 (batch 2) and protease variant 3 (batch 3). The alkaline protease from Bacillus gibsonii DSM 14391 according to SEQ ID NO. 1 was used as the standard.

After washing, the whiteness of the washed textiles was measured. The measurement was performed using a Minolta CM508d spectrometer (illuminant D65, 10°). The instrument was calibrated in advance with a white standard supplied with the instrument. The results obtained are the relative performances of the proteases according to the invention compared with the standard protease (measured in Y units) and are summarized in Table 1 below. They allow a direct conclusion to be drawn regarding the contribution of the enzyme contained in the agent that was used to the cleaning performance of the agent.

TABLE 1

Washing results with a powdered washing agent at 20° C. or 40° C.

|  | Standard | Batch 1 | Batch 2 | Batch 3 |
|---|---|---|---|---|
| 20° C. | 100% | 178% | 246% | 250% |
| 40° C. | 100% | 171% | 218% | 220% |

It is clear that the proteases according to the invention have an advantageous cleaning performance.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A protein comprising a protease which is at least 90% identical to SEQ ID NO. 1 over the full-length and comprises the substitution corresponding to I21V of SEQ ID NO. 1, and further comprising at least one further amino acid substitution corresponding to Q12L, M122L, N177V, A222S, V2228I or T247N of SEQ ID NO. 1.

2. A protein comprising a protease according to claim 1, wherein a starting protease has been fragmented and wherein a fragment of the starting protease, over a length of at least 50 successive amino acids, matches the starting protease and one or more fragments of the starting protease, either individually and/or as a complex, expresses protease activity.

3. A protein comprising a protease according to claim 1, wherein a number of additional amino acid substitutions replace an amino acid of SEQ ID NO. 1 with the different amino acid of SEQ ID NO. 3 at the same position.

4. A nucleic acid that codes for a protein containing a protease according to claim 1.

5. A vector containing a nucleic acid according to claim 4.

6. An isolated non-human host cell containing a nucleic acid according to claim 4.

7. A method for producing a protease, encompassing:
 a) cultivating the host cell according to claim 6 and
 b) isolating the protease from the host cell.

8. An agent comprising from 2 μg to 20 mg of protein containing a protease according to claim 1, per gram of agent.

9. An agent comprising from 2 μg to 20 mg of protein containing a protease according to claim 1, per gram of agent, wherein the protein is encapsulated by a substance that is impermeable for the protease at room temperature in the absence of water.

10. The protein comprising a protease according to claim 2, in which a fragment dissociates from the protease, and the protease remains active, wherein protease activity is provided by one or more fragments of the protease that is at least 90% identical to SEQ NO. 1.

11. The protein comprising a protease according to claim 1, in which the protease is at least 95% identical to SEQ ID NO. 1 over the entire length thereof.

12. The protein comprising a protease according to claim 1, wherein the protease is defined by SEQ ID. NO. 4.

13. The protein comprising a protease according to claim 1, wherein the protease is defined by SEQ ID. NO. 5.

14. The protein comprising a protease according to claim 1, wherein the protease is defined by SEQ ID. NO. 6.

* * * * *

SEQUENCE LISTING

<160> NUMBER OF SEQ ID NOS: 6

<210> SEQ ID NO 1
<211> LENGTH: 269
<212> TYPE: PRT
<213> ORGANISM: Bacillus sp.

<400> SEQUENCE: 1

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

```
Val Ala Pro Gly Val Gly Ile Gln Ser Thr Tyr Leu Asn Asn Ser Tyr
            195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
            245                 250                 255

Phe Gly Ser Gly Leu Val Asn Ala Asp Ala Ala Thr Arg
            260                 265

<210> SEQ ID NO 2
<211> LENGTH: 269
<212> TYPE: PRT
<213> ORGANISM: Bacillus sp.

<400> SEQUENCE: 2

Gln Gln Thr Val Pro Trp Gly Ile Thr Arg Val Gln Ala Pro Thr Val
1               5                   10                  15

His Asn Arg Gly Val Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 3
<211> LENGTH: 269
<212> TYPE: PRT
```

<213> ORGANISM: Bacillus lentus

<400> SEQUENCE: 3

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
195 200 205

Ala Ser Leu Asn Gly Thr Ser Met Ala Thr Pro His Val Ala Gly Ala
210 215 220

Ala Ala Leu Val Lys Gln Lys Asn Pro Ser Trp Ser Asn Val Gln Ile
225 230 235 240

Arg Asn His Leu Lys Asn Thr Ala Thr Ser Leu Gly Ser Thr Asn Leu
245 250 255

Tyr Gly Ser Gly Leu Val Asn Ala Glu Ala Ala Thr Arg
260 265

<210> SEQ ID NO 4
<211> LENGTH: 269
<212> TYPE: PRT
<213> ORGANISM: Bacillus sp.

<400> SEQUENCE: 4

Gln Gln Thr Val Pro Trp Gly Ile Thr Arg Val Gln Ala Pro Thr Val
1 5 10 15

His Asn Arg Gly Val Thr Gly Ser Gly Val Lys Val Ala Ile Leu Asp
20 25 30

Thr Gly Ile Ala Gln His Ser Asp Leu Thr Ile Arg Gly Gly Ala Ser
35 40 45

Phe Val Pro Gly Glu Ser Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Ser Ala Asp Leu Tyr Ala Val Lys Val Leu Gly Ala

```
            85                  90                  95
Asn Gly Arg Gly Ser Val Ser Gly Ile Ala Gln Gly Leu Glu Trp Ala
            100                 105                 110
Ala Thr Asn Asn Met His Ile Ala Asn Leu Ser Leu Gly Ser Asp Ala
            115                 120                 125
Pro Ser Thr Thr Leu Glu Arg Ala Val Asn Tyr Ala Thr Ser Arg Gly
        130                 135                 140
Val Leu Val Ile Ala Ala Thr Gly Asn Gly Thr Gly Ser Ile Gly
145                 150                 155                 160
Tyr Pro Ala Arg Tyr Ala Asn Ala Met Ala Val Gly Ala Thr Asp Gln
                165                 170                 175
Asn Asn Arg Arg Ala Ser Phe Ser Gln Tyr Gly Thr Gly Ile Asp Ile
            180                 185                 190
Val Ala Pro Gly Val Gly Ile Gln Ser Thr Tyr Leu Asn Asn Ser Tyr
        195                 200                 205
Ala Ser Met Pro Gly Thr Ser Met Ala Thr Pro His Val Ser Gly Val
        210                 215                 220
Ala Ala Leu Val Lys Gln Lys Asn Pro Ser Trp Asn Ala Thr Gln Ile
225                 230                 235                 240
Arg Asn His Leu Lys Asn Asn Ala Thr Asn Leu Gly Asn Ser Ser Gln
                245                 250                 255
Phe Gly Ser Gly Leu Val Asn Ala Asp Ala Ala Thr Arg
            260                 265

<210> SEQ ID NO 5
<211> LENGTH: 269
<212> TYPE: PRT
<213> ORGANISM: Bacillus sp.

<400> SEQUENCE: 5

Gln Gln Thr Val Pro Trp Gly Ile Thr Arg Val Gln Ala Pro Thr Val
1               5                   10                  15
His Asn Arg Gly Val Thr Gly Ser Gly Val Lys Val Ala Ile Leu Asp
            20                  25                  30
Thr Gly Ile Ala Gln His Ser Asp Leu Thr Ile Arg Gly Gly Ala Ser
        35                  40                  45
Phe Val Pro Gly Glu Ser Thr Thr Ala Asp Leu Asn Gly His Gly Thr
    50                  55                  60
His Val Ala Gly Thr Val Ala Ala Leu Asn Asn Ser Ile Gly Val Ile
65                  70                  75                  80
Gly Val Ala Pro Ser Ala Asp Leu Tyr Ala Val Lys Val Leu Gly Ala
                85                  90                  95
Asn Gly Arg Gly Ser Val Ser Gly Ile Ala Gln Gly Leu Glu Trp Ala
            100                 105                 110
Ala Thr Asn Asn Met His Ile Ala Asn Met Ser Leu Gly Ser Asp Ala
            115                 120                 125
Pro Ser Thr Thr Leu Glu Arg Ala Val Asn Tyr Ala Thr Ser Arg Gly
        130                 135                 140
Val Leu Val Ile Ala Ala Thr Gly Asn Asn Gly Thr Gly Ser Ile Gly
145                 150                 155                 160
Tyr Pro Ala Arg Tyr Ala Asn Ala Met Ala Val Gly Ala Thr Asp Gln
                165                 170                 175
Val Asn Arg Arg Ala Ser Phe Ser Gln Tyr Gly Thr Gly Ile Asp Ile
            180                 185                 190
```

```
Val Ala Pro Gly Val Gly Ile Gln Ser Thr Tyr Leu Asn Asn Ser Tyr
            195                 200                 205

Ala Ser Met Pro Gly Thr Ser Met Ala Thr Pro His Val Ala Gly Val
        210                 215                 220

Ala Ala Leu Ile Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 6
<211> LENGTH: 269
<212> TYPE: PRT
<213> ORGANISM: Bacillus sp.

<400> SEQUENCE: 6

Gln Gln Thr Val Pro Trp Gly Ile Thr Arg Val Leu Ala Pro Thr Val
1               5                   10                  15

His Asn Arg Gly Val Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Leu Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ser Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265
```